United States Patent [19]

Shoshan et al.

[11] Patent Number: 5,514,657
[45] Date of Patent: May 7, 1996

[54] TOPICAL ANTIBACTERIAL PREPARATION

[75] Inventors: Shmuel Shoshan, Motza Elit; David Marcos, Kibbutz Maabarot, both of Israel

[73] Assignee: Yissum Research Development Company of the Hebrew University, Jerusalem, Israel

[21] Appl. No.: 337,377

[22] Filed: Nov. 8, 1994

[30] Foreign Application Priority Data

Nov. 11, 1993 [IL] Israel .......................................... 107578

[51] Int. Cl.⁶ ........................... A61K 38/00; A61K 38/17; A61K 31/74
[52] U.S. Cl. .......................... 514/21; 514/801; 514/886; 514/887; 530/356; 424/78.06; 424/78.07; 424/520; 424/DIG. 13
[58] Field of Search ............................. 514/21, 801, 886, 514/887; 530/356; 424/78.06, 78.07, 520, DIG. 13

[56] References Cited

U.S. PATENT DOCUMENTS

| | | | |
|---|---|---|---|
| 3,800,792 | 4/1974 | McKnight et al. | 128/156 |
| 4,581,028 | 4/1986 | Fox, Jr. et al. | 623/2 |
| 4,599,226 | 7/1986 | Fox, Jr. et al. | 424/27 |
| 4,915,694 | 4/1990 | Yamamoto et al. | 604/180 |

FOREIGN PATENT DOCUMENTS

| | | |
|---|---|---|
| 140596 | 5/1985 | European Pat. Off. . |
| 0251783 | 1/1988 | European Pat. Off. . |
| 301977 | 2/1989 | European Pat. Off. . |
| 0411124 | 2/1991 | European Pat. Off. . |
| 480189 | 4/1992 | European Pat. Off. . |
| 3523023 | 1/1987 | Germany . |
| WO91/15233 | 10/1991 | WIPO . |

OTHER PUBLICATIONS

Popovici et al., *Chemical Abstracts*, vol. 112, p. 415, Ref. No. 164844k, 1990 (Farmacia (Bucharest) 1988, 36(4), 207–216).

Zachary et al., *Biological Abstracts*, vol. 76, Ref. #47459,83 (J. Trauma, 22(10), 1982, 833–836).

Abstract, vol. 112, No. 18, 30 Apr. 1990, Columbus, OH, US: Abstract No. 164844, Iuliana et al. 'Studies on Collagen Gels containing silver sulfamethoxydiazine used in Dermatology and Farmacia vol. 36, No. 4, 1988 pp. 207–216.

Minerva Chirurgica vol. 49, No. 5, May 1994, pp. 377–382
The Journal of Trauma, vol. 22 No. 10, Oct. 1982, pp. 833–836.

Popovici et al. *Farmacia*, vol. 36, nr. 4, pp. 207–217, 1988.

*Primary Examiner*—Christina Y. Chan
*Assistant Examiner*—Abdel A. Mohamed
*Attorney, Agent, or Firm*—Jacobson, Price, Holman & Stern

[57] ABSTRACT

A topical antibacterial preparation for treating infected wounds and for advancing their healing comprises silver sulfadiazine (SSD) and collagen, in which the w/w ratio of collagen to SSD ranges from 4/1 to 200/1. The concentration of the SSD is preferably from 0.5% to 2.5%, advantageously 1%. The collagen is advantageously native collagen, which may be acid soluble or insoluble, or mixtures thereof. The preparation may comprise an inert excipient, e.g. $SiO_2$, or blood plasma components, peptides, carbohydrates.

11 Claims, No Drawings

TOPICAL ANTIBACTERIAL PREPARATION

FIELD OF THE INVENTION

The present invention relates to a topical antibacterial preparation for the treatment of infected wounds and for the enhancement of their healing.

BACKGROUND

Silver sulfadiazine (SSD) preparations are among the best topical antibacterial agents in clinical use for the treatment of infected wounds, especially of burns. However, because SSD is water-insoluble, its most commonly known preparations consist of dispersions with water-soluble cream bases containing, inter alia, emulsifying substances that not only do not contribute to the healing process but frequently even hinder it. Moreover, said known preparations cannot be used in a dry form. Finally the amount of SSD required in said emulsions, as suggested by various manufacturers, is about 318–530 mg in an area of 10×10 cm in a 3–5 mm layer. These large amounts of SSD may cause systemic absorption and damage to the wound tissue.

From European Patent Specification B 140,596 there is known a porous complex of a biodegradable fibrous protein, e.g. collagen, with a polyanionic plant, polysaccharide. S.S.D. may be incorporated into the wound contact layer. It should be stressed that there is concerned a complex and not a simple mixture and/or compound which requires the presence of a special polysaccharide. Said polysaccharide gives special properties to the complex which are described and claimed.

Collagen is the major connective tissue structural protein with a variety of biological properties that are intimately involved in all phases of tissue repair processes following injury. The collagen molecule has several hydrophobic domains along its long polypeptide chains which are suitable for hydrophobic interactions with other hydrophobic molecules, such as silver sulfadiazine.

From U.S. Pat. No. 4,581,028 is known an infection-resistant device which is a vascular graft prosthesis for use within the interior of a human or animal body which may comprise collagen and SSD. However, said device cannot be used as a topical preparation. However, the amount of SSD utilised cannot be calculated.

From U.S. Pat. No. 4,599,226 is known a method for preparing animal tissues for use as burn or wound dressings comprising, inter alia, SSD. It is assumed that collagen may be present in the skin tissue utilised. However, nothing can be learned about a topical preparation comprising collagen and SSD.

From DOS3.523.023 A1 is known a collagen sponge comprising 0.5–10 mg of a silver salt which dissolves with difficulty. However, only the use of inorganic silver salts is shown and a very specific method of preparation is exemplified.

It has thus been desirable to find a specific topical preparation which overcomes the above disadvantages, should be easy to prepare and have the required amounts of SSD.

SUMMARY OF THE INVENTION

It has been found that, by interacting collagen with SSD, one has no need to use emulsifying agents, thus obtaining an active antibacterial preparation which also enhances the healing process at the same time.

The present invention thus consists in a composition comprising silver sulfadiazine (SSD) and collagen, in which the ratio (w/w) of collagen to SSD ranges from 4 parts collagen to 1 part SSD to 200 parts collagen to 1 part SSD.

DETAILS

A preferred composition according to the present invention comprises 0.5%–2.5% of SSD, advantageously about 1%.

In a preferred embodiment of the invention said composition comprises an inert excipient, e.g. colloidal silver dioxide ($SiO_2$).

The collagen indicated herein is preferably native collagen of type I, which may be either pure or comprise other types of collagen, e.g. type III, and in which the triple helical conformation of the molecule is preserved. The native collagen may be acid soluble (ASC) or insoluble (ISC) or a combination of both.

The ACS can be prepared from any source that is rich in type I, such as, tendons, bovine or goat hide, human placenta, etc. A preferred source is bovine hide.

Suitable methods for the preparation of ASC are described in The Methodology of Connective Tissue Research, edited by David A. Hall, Chapter 3,—Preparation of Acid and Citrate Soluble Collagen.

A specific method is described by J. Gross (J. Exp. Med. 107: 247–263, 1958), but as indicated above, other methods are also suitable.

There are known various methods to prepare ISC. Suitable methods are described in the above book edited by David A. Hall, chapter 1, Z. Deyl and M. Adam, pages 1–8. A suitable method is described in European Patent Application No. 301,977. However, there may also be indicated further ones, such as a collagen cross-linked with starch dialdehyde.

Specific methods are described also in (1) Bairati, A. et al.— J. Submicr. Cytol 4: 89, 1972; (2) Gupta, R. L. et al.—Indian J. Surg. 646, 1978; (3) Woodroof, E. A.—J. Bioeng. 2: 1, 1078; and (4) Chvapil, M. et al.—J. Surg. Res. 35: 402, 1983.

The composition according to the present invention may be used in the dry form or in a liquid form. It may comprise additional materials, e.g. blood plasma components, peptides, carbohydrates, etc. The composition according to the present invention is suitably prepared by adding, with constant stirring, the required amount of SSD admixed with $SiO_2$, if present, to an appropriate cold (0°–4° C.) solution of the collagen in 0.1–0.5M acetic acid. This is then followed by mild vortexing the composition obtained for about 10–15 minutes, after which it is lyophilized, sterilized and stored under suitable conditions.

The sterilization is performed preferably by gamma irradiation.

The composition according to the present invention may also be prepared in the form suitable for reconstitution as a liquid preparation. After preparation as described above, the lyophilized material is dissolved in 0.1–0.5M acetic acid and then dialyzed against a suitable buffer (e.g. Na or K phosphate buffer, TRIS buffer) adjusted to pH 7.4–7.6. The preparation is lyophilized, suitably packed and sterilized. It is then ready for reconstitution by the addition of an appropriate quantity of sterile purified water.

The present invention will now be illustrated with reference to the following Examples without being limited by them. In all Examples 1–3, collagen stands for native collagen.

EXAMPLE 1

The following composition was prepared:

| | |
|---|---|
| SSD | 1% |
| Colloidal Silicon Dioxide | 0.05% |
| (Aerosil 300 Degussa, Germany) | |
| Collagen | to 100% |

The composition was prepared as follows:

The SSD was mixed with the Aerosil and the mixture was dispersed in a 0.5M Acetic Acid solution of Collagen. The preparation was subsequently dried by lyophilization.

a. (ASP)

The preparation (ASP) consisted of a powder in which mainly acid soluble type I collagen was used.

b. (ASS)

The preparation (ASS) consisted of a sponge in which mainly acid soluble type I collagen was used. Said sponge was weighed and measured. The specific gravity was approximately 0.0107 g/cc. Such a sponge of 0.3 cm thickness and 10×10 cm area contains about 3.2 mg SSD.

c. (ISP)

The preparation (ISP) consisted of a powder in which mainly insoluble type I collagen was used.

d. (ISS)

The preparation (ISS) consisted of a sponge in which mainly insoluble type I collagen was used.

Results of Tests Performed with Examples a–d

A) In vitro tests were performed to determine the bacteriostatic and bacteriocidal properties of the preparations. The object of this study was to test whether the SSD in said preparations would still show its antibacterial activity in vitro.

Samples of each of the four preparations were placed as isolated foci on Blood-Agar plates which were seeded with either *Pseudomonas aeruginosa*, *Escherichia coli* or *Staphylococcus aureus*. The growth of the microorganisms was monitored after incubation for 24 and 48 hours. Bacterial growth was inhibited around all the samples containing SSD. The tests were repeated in several different variations, all with the same results, indicating an effective inhibition of bacterial growth (bacteriostasis) or an effective control of a contaminated field (bacteriocidal activity).

All the samples containing collagen with SSD were thus found to be equally effective as both infection-preventing and infection-combating agents in vitro.

B) Preliminary in vivo studies were performed to test the effect of the different preparations on the healing process of non-infected dermal wounds.

The object of this study was to ascertain that the various preparations, when placed on wounds, did not impair the healing process.

Full-thickness dermal excision wounds were inflicted on the back of anaesthetized guinea pigs, which were then treated with either of said preparations, or left untreated. An equal amount of either preparation was placed on the wound. The results were assessed histologically after 10 days. They showed that none of the preparations had a deleterious effect on the healing process. Moreover, healing was even enhanced with the preparations containing SSD as compared to those left untreated. The rate of closure was as follows:

| | |
|---|---|
| Control (untreated) | 50% closure |
| ASS | 60% closure |
| ISS | 80% closure |
| ISP | 80% closure |
| ASP | 100% closure |

C) Preliminary in vivo studies were performed on the effect of the different preparations on the bacterial count in infected wounds.

The object of this study was to test the ability of the preparations to reduce the bacterial count in infected wounds in vivo.

Full-thickness dermal excision wounds were inflicted on the back of anaesthetized guinea pigs and infected with about $1\times10^6$ bacteria. After 30 minutes the wounds were covered with either of said preparations, or left untreated. Bacterial counts were performed on day 1, day 3, day 7 and day 10. At each time point, the wound samples were treated with a Stomacher Lab Blender and the number of viable bacteria in the wound were counted by the agarplate method. In all the samples from wounds treated with preparations containing SSD there was a drastic and significant drop in the bacterial count lasting 7 to 10 days, as compared with the untreated contaminated wounds.

EXAMPLE 2

The following composition was prepared:

| | |
|---|---|
| Silver Sulfadiazine | 5% |
| Aerosil 300 | 0.25% |
| Collagen | to 100% |

The Silver Sulfadiazine was mixed with the Aerosil and the mixture was dispersed in a 0.5% M Acetic Acid solution of Collagen. The preparation was subsequently lyophilized. In vitro tests to determine the antibacterial activity were carried out. Samples of the preparation were placed as isolated foci on Mueller Hinton agar plates which were seeded with either *Escherichia coli* or *Staphylococcus aureus*. The growth of the microorganisms was monitored for 24 and 48 hours. Bacterial growth was inhibited around all the samples.

EXAMPLE 3

The following composition was prepared:

| | |
|---|---|
| Silver Sulfadiazine | 20% |
| Aerosil 300 | 1% |
| Collagen | to 100% |

The Silver Sulfadiazine was mixed with Aerosil and the mixture was dispersed in a 0.5% M Acetic Acid solution of Collagen. The preparation was subsequently lyophilized. In vitro tests to determine the antibacterial activity were carried out. Samples of the preparation were placed as isolated foci on Mueller Hinton agar plates which were seeded with either *Escherichia coli* or *Staphylococcus aureus*. The growth of the microorganisms was monitored for 24 and 48 hours. Bacterial growth was inhibited around all the samples.

We claim:

1. A composition comprising silver sulfadiazine (SSD) and collagen in which the ratio w/w of collagen to SSD ranges from 4 parts collagen to 1 part SSD to 200 parts collagen to 1 part SSD.

2. A composition of claim 1 wherein SSD and collagen are the sole essential active components.

3. A composition according to claim 1, wherein the concentration of SSD in the preparation ranges from 0.5% to 2.5%.

4. A composition according to claim 3, wherein said concentration is 1%.

5. A composition according to claim 1, wherein the collagen is mainly native collagen.

6. A composition according to claim 5, wherein the native collagen is acid soluble collagen (ASC).

7. A composition according to claim 5, wherein the native collagen is insoluble collagen (ISC).

8. A composition according to claim 5, wherein the native collagen is a mixture of ASC and ISC.

9. A composition according to claim 1, further comprising colloidal silicon dioxide.

10. A method for enhancing wound healing which comprises topically applying to a wound an effective amount of a composition according to claim 1.

11. A method of treating an infected wound which comprises topically applying thereto an effective amount of a composition according to claim 1.

* * * * *